(12) United States Patent
Ando et al.

(10) Patent No.: US 8,730,550 B2
(45) Date of Patent: May 20, 2014

(54) DISPLAY DEVICE

(75) Inventors: Naohisa Ando, Mobara (JP); Masataka Okamoto, Chosei-gun (JP); Takahiko Muneyoshi, Chiba (JP)

(73) Assignee: Pixtronix, Inc., San Diego, CA (US)

( * ) Notice: Subject to any disclaimer, the term of this patent is extended or adjusted under 35 U.S.C. 154(b) by 91 days.

(21) Appl. No.: 13/565,835

(22) Filed: Aug. 3, 2012

(65) Prior Publication Data

US 2013/0038918 A1  Feb. 14, 2013

(30) Foreign Application Priority Data

Aug. 11, 2011  (JP) .................................. 2011-175478

(51) Int. Cl.
*G02B 26/02*  (2006.01)
(52) U.S. Cl.
USPC ............................................ 359/228; 345/84
(58) Field of Classification Search
USPC .................... 359/228; 345/7, 55, 84
See application file for complete search history.

(56) References Cited

U.S. PATENT DOCUMENTS 7,738,344 B2 * 6/2010 Ooi et al. ................. 369/112.02
2006/0250325 A1  11/2006 Hagood et al.

FOREIGN PATENT DOCUMENTS

JP  2008-197668  8/2008

* cited by examiner

*Primary Examiner* — James Phan
(74) *Attorney, Agent, or Firm* — Edward A. Gordon; Foley & Lardner LLP

(57) ABSTRACT

Provided is a display device, including: a pair of light transmissive substrates disposed to be opposed to each other at an interval; a sealing member which bonds the pair of light transmissive substrates together and defines an encapsulation space between the pair of light transmissive substrates; a plurality of shutters disposed in the encapsulation space so as to optically display an image; liquid having optical isotropy filled in the encapsulation space; and an optical film disposed between the liquid and at least one of the pair of light transmissive substrates. A refractive index of the optical film is different from a refractive index of the pair of light transmissive substrates.

19 Claims, 4 Drawing Sheets

$n_o < n_1 > n_2$

DISPLAY DEVICE

CROSS-REFERENCE TO RELATED APPLICATION

The present application claims priority from Japanese application JP 2011-175478 filed on Aug. 11, 2011, the content of which is hereby incorporated by reference into this application.

BACKGROUND OF THE INVENTION

1. Field of the Invention

The present invention relates to a display device, and more particularly, to a display device which uses micro-electro-mechanical systems (MEMS) for pixels.

2. Description of the Related Art

A micro-electro-mechanical system (MEMS) display is a display expected to replace a liquid crystal display (see Japanese Patent Application Laid-open No. 2008-197668). This display differs from a liquid crystal shutter type display utilizing polarization, and performs light-dark display by opening and closing a light transmissive window using a mechanical shutter system. A mechanical shutter (hereinafter, simply referred to as shutter) is formed of an amorphous silicon film. Vertical and horizontal sizes of one shutter forming one pixel are in the order of several hundred micrometers, and a thickness thereof is in the order of several micrometers. One shutter is opened/closed to enable ON/OFF operation for one pixel. The shutter is operated by an electrostatic attractive force.

Oil is filled inside a panel in which the shutter operates, and the oil increases the dielectric constant in the panel, to thereby reduce a voltage necessary for driving the shutter. The oil is sealed by a sealing agent, but the oil may leak due to exfoliation or damage of the sealing agent. When the oil leaks, an air bubble may be generated in the panel (region filled with the oil). However, a difference of color between the region filled with the oil and a region in which an air bubble is generated is very small, and visual inspection of the difference, namely visual inspection of presence of an air bubble is difficult.

SUMMARY OF THE INVENTION

It is an object of the present invention to facilitate inspection of an air bubble generated in filled liquid.

(1) According to an exemplary embodiment of the present invention, there is provided a pair of light transmissive substrates disposed to be opposed to each other at an interval; a sealing member which bonds the pair of light transmissive substrates together and defines an encapsulation space between the pair of light transmissive substrates; a plurality of shutters disposed in the encapsulation space so as to optically display an image; liquid having optical isotropy filled in the encapsulation space; and an optical film disposed between the liquid and at least one of the pair of light transmissive substrates, in which: one surface of the optical film is provided in contact with the liquid; another surface of the optical film is provided in contact with one of the pair of light transmissive substrates; and a refractive index of the optical film is different from a refractive index of the one of the pair of light transmissive substrates provided in contact with the optical film. In simulation, there was disposed an optical film having a refractive index different from that of the light transmissive substrate, and then it was found that a difference of reflection factor between light passing through the liquid and light passing through an air bubble was increased when the air bubble was generated in the liquid. According to the exemplary embodiment of the present invention, it is easy to inspect the air bubble by the difference of reflection factor.

(2) In the display device according to Item (1), the optical film may be formed of a single layer.

(3) In the display device according to Item (1), the optical film may be formed of a plurality of layers.

(4) In the display device according to any one of Items (1) to (3), the refractive index of the optical film may be larger than the refractive index of the one of the pair of light transmissive substrates provided in contact with the optical film and may be larger than refractive indices of air and the liquid.

(5) In the display device according to any one of Items (1) to (4), the optical film may be disposed so that a lower surface thereof is adjacent to the one of the pair of light transmissive substrates, and when natural light irradiates an upper surface of the optical film, reflection light that is reflected by the upper surface and propagates may interfere with reflection light that enters the optical film and is reflected by the lower surface so as to exit from the upper surface.

(6) In the display device according to any one of Items (1) to (4), the optical film may be disposed so that an upper surface thereof is adjacent to the one of the pair of light transmissive substrates, and when natural light irradiates the upper surface, reflection light that is reflected by the upper surface and propagates may interfere with reflection light that enters the optical film and is reflected by a lower surface of the optical film so as to exit from the upper surface.

(7) In the display device according to any one of Items (1) to (4): the optical film may include a first optical film and a second optical film; each of the first optical film and the second optical film may have an upper surface and a lower surface; the lower surface of the first optical film may be adjacent to one of the pair of light transmissive substrates; the upper surface of the second optical film may be adjacent to another of the pair of light transmissive substrates; and when natural light irradiates each of the upper surface of the first optical film and the upper surface of the second optical film, reflection light that is reflected by the upper surface of the first optical film and propagates may interfere with reflection light that enters the first optical film and is reflected by the lower surface of the first optical film so as to exit from the upper surface of the first optical film, while reflection light that is reflected by the upper surface of the second optical film and propagates may interfere with reflection light that enters the second optical film and is reflected by the lower surface of the second optical film so as to exit from the upper surface of the second optical film.

(8) In the display device according to Item (5): the following expressions may hold: $n_0 < n_1$ and $n_2 < n_1$, where $n_0$ represents a refractive index of a substance adjacent to the upper surface of the optical film, $n_1$ represents the refractive index of the optical film, and $n_2$ represents the refractive index of the one of the pair of light transmissive substrates provided in contact with the optical film; the natural light may include a light ray group including light rays having different wavelengths and different incident angles to the optical film; a light ray group having a wavelength $\lambda_0$ included in the natural light may include a first light ray reflected by the upper surface and a second light ray reflected by the lower surface so as to exit from the upper surface; when an optical path difference between the first light ray and the second light ray is an odd multiple of half the wavelength $\lambda_0$, a reflection factor of the first light ray and the second light ray may become a maximum value determined by $Rmax = ((n_0 n_2 - n_1^2)/(n_0 n_2 + n_1^2))^2$; when the optical path difference between the first light ray and the second light ray is an integral multiple of the wavelength $\lambda_0$, the reflection factor of the first light ray and the second light ray may become a minimum value determined by $Rmin=((n_0-n_2)/(n_0+n_2))^2$; a reflection factor of the natural light when the natural light passes through the liquid may be in a range from a minimum reflection factor $R_{LIQUID}min$ to a maximum reflection factor $R_{LIQUID}max$ obtained by substituting a refractive index of the liquid into $n_0$ in equations for determining the minimum value and the maximum value; a reflection factor of the natural light when the liquid includes an air bubble on the optical film and the natural light passes through the air bubble may be in a range from a minimum reflection factor $R_{Air}min$ to a maximum reflection factor $R_{Air}max$ obtained by substituting a refractive index of air into $n_0$ in the equations for determining the minimum value and the maximum value; and one of an average value of the minimum reflection factor $R_{Air}min$ and the maximum reflection factor $R_{Air}max$ and an average value of the minimum reflection factor $R_{LIQUID}Min$ and the maximum reflection factor $R_{LIQUID}max$ may be larger than twice another thereof.

(9) In the display device according to Item (6): the following expressions may hold: $n_0<n_1$ and $n_2<n_1$, where $n_0$ represents a refractive index of a substance adjacent to the lower surface of the optical film, $n_1$ represents the refractive index of the optical film, and $n_2$ represents the refractive index of the one of the pair of light transmissive substrates provided in contact with the optical film; the natural light may include a light ray group including light rays having different wavelengths and different incident angles to the optical film; a light ray group having a wavelength $\lambda_0$ included in the natural light may include a first light ray reflected by the upper surface and a second light ray reflected by the lower surface so as to exit from the upper surface; when an optical path difference between the first light ray and the second light ray is an odd multiple of half the wavelength $\lambda_0$, a reflection factor of the first light ray and the second light ray may become a maximum value determined by $Rmax=((n_2n_0-n_1^2)/(n_2n_0+n_1^2))^2$; when the optical path difference between the first light ray and the second light ray is an integral multiple of the wavelength $\lambda_0$, the reflection factor of the first light ray and the second light ray may become a minimum value determined by $Rmin=((n_2-n_0)/(n_2+n_0))^2$; a reflection factor of the natural light when the natural light is reflected by the upper surface and the lower surface above the liquid may be in a range from a minimum reflection factor $R_{LIQUID}min$ to a maximum reflection factor $R_{LIQUID}max$ obtained by substituting a refractive index of the liquid into $n_0$ in equations for determining the minimum value and the maximum value; a reflection factor of the natural light when the liquid includes an air bubble on the optical film and the natural light is reflected by the upper surface and the lower surface above the air bubble may be in a range from a minimum reflection factor $R_{Air}min$ to a maximum reflection factor $R_{Air}max$ obtained by substituting a refractive index of air into $n_0$ in the equations for determining the minimum value and the maximum value; and one of an average value of the minimum reflection factor $R_{Air}min$ and the maximum reflection factor $R_{Air}max$ and an average value of the minimum reflection factor $R_{LIQUID}min$ and the maximum reflection factor $R_{LIQUID}max$ may be larger than twice another thereof.

(10) In the display device according to Item (7): the following expressions may hold: $n_0<n_1$ and $n_2<n_1$, where $n_0$ represents a refractive index of a substance adjacent to the upper surface of the first optical film and the lower surface of the second optical film, $n_1$ represents a refractive index of the first optical film, and $n_2$ represents a refractive index of the one of the pair of light transmissive substrates provided in contact with the first optical film; the following expressions may hold: $n_0<n_{12}$ and $n_{22}<n_{12}$, where $n_{12}$ represents a refractive index of the second optical film, and $n_{22}$ represents a refractive index of the another of the pair of light transmissive substrates provided in contact with the second optical film; the natural light may include a light ray group including light rays having different wavelengths and different incident angles to the first optical film and the second optical film; a light ray group having a wavelength $\lambda_0$ included in the natural light may include a first light ray reflected by the upper surface of the first optical film, a second light ray reflected by the lower surface of the first optical film so as to exit from the upper surface of the first optical film, a third light ray reflected by the upper surface of the second optical film, and a fourth light ray reflected by the lower surface of the second optical film so as to exit from the upper surface of the second optical film; when an optical path difference between the first light ray and the second light ray is an odd multiple of half the wavelength $\lambda_0$, a reflection factor of the first light ray and the second light ray on the upper surface and the lower surface of the first optical film may become a first maximum value determined by $Rmax=((n_0n_2-n_1^2)/(n_0n_2+n_1^2))^2$; when the optical path difference between the first light ray and the second light ray is an integral multiple of the wavelength $\lambda_0$, the reflection factor of the first light ray and the second light ray on the upper surface and the lower surface of the first optical film may become a first minimum value determined by $Rmin=((n_0-n_2)/(n_0+n_2))^2$; a reflection factor of the natural light on the upper surface and the lower surface of the first optical film when the natural light passes through the liquid may be in a range from a minimum reflection factor $R_{LIQUID}min$ to a maximum reflection factor $R_{LIQUID}max$ obtained by substituting a refractive index of the liquid into $n_0$ in equations for determining the first minimum value and the first maximum value; a reflection factor of the natural light on the upper surface and the lower surface of the first optical film when the liquid includes an air bubble on the first optical film and the natural light passes through the air bubble may be in a range from a minimum reflection factor $R_{Air}min$ to a maximum reflection factor $R_{Air}max$ obtained by substituting a refractive index of air into $n_0$ in the equations for determining the first minimum value and the first maximum value; an average value of the minimum reflection factor $R_{Air}min$ and the maximum reflection factor $R_{Air}max$ may be larger than twice an average value of the minimum reflection factor $R_{LIQUID}min$ and the maximum reflection factor $R_{LIQUID}max$; when an optical path difference between the third light ray and the fourth light ray is an odd multiple of half the wavelength $\lambda_0$, a reflection factor of the third light ray and the fourth light ray on the upper surface and the lower surface of the second optical film may become a second maximum value determined by $Rmax_2=((n_{22}n_0-n_{12}^2)/(n_{22}n_0+n_{12}^2))^2$; when the optical path difference between the third light ray and the fourth light ray is an integral multiple of the wavelength $\lambda_0$, the reflection factor of the third light ray and the fourth light ray on the upper surface and the lower surface of the second optical film may become a second minimum value determined by $Rmin_2=((n_{22}-n_0)/(n_{22}+n_0))^2$; a reflection factor of the natural light on the upper surface and the lower surface of the second optical film when the natural light is reflected above the liquid may be in a range from a minimum reflection factor $R_{LIQUID}min_2$ to a maximum reflection factor $R_{LIQUID}max_2$ obtained by substituting the refractive index of the air into $n_0$ in equations for determining the second minimum value and the second maximum value; a reflection factor of the natural light on the upper surface and the lower surface of the second optical film when the natural light is reflected above the air bubble may be in a range from a minimum reflection factor $R_{Air}\min_2$ to a maximum reflection factor $R_{Air}\max_2$ obtained by substituting the refractive index of the air into $n_0$ in the equations for determining the second minimum value and the second maximum value; and one of an average value of the minimum reflection factor $R_{Air}\min_2$ and the maximum reflection factor $R_{Air}\max_2$ and an average value of the minimum reflection factor $R_{LIQUID}\min_2$ and the maximum reflection factor $R_{LIQUID}\max_2$ may be larger than twice another thereof.

(11) In the display device according to any one of Items (1) to (10), the sealing member may be disposed so as to avoid a periphery of the pair of light transmissive substrates, and the periphery of the pair of light transmissive substrates may extend outward from the sealing member.

(12) In the display device according to Item (11), the sealing member may be disposed so as to avoid an entirety of the periphery of the pair of light transmissive substrates, and the entirety of the periphery of the pair of light transmissive substrates may extend outward from the sealing member.

(13) In the display device according to Item (11): the sealing member may be disposed so as to avoid a first part of the periphery of the pair of light transmissive substrates, and so as to pass a second part of the periphery of the pair of light transmissive substrates; and the first part of the periphery of the pair of light transmissive substrates may extend outward from the sealing member.

(14) In the display device according to any one of Items (1) to (10): each of the pair of light transmissive substrates may have a rectangular shape in plan view; the sealing member may be disposed so as to avoid a corner of the pair of light transmissive substrates; and the corner of the pair of light transmissive substrates may extend outward from the sealing member.

(15) In the display device according to any one of Items (1) to (14), the optical film may be disposed at least in a part adjacent to the sealing member in a region surrounded by the sealing member.

(16) In the display device according to Item (15), the optical film may be disposed in an entire region surrounded by the sealing member.

(17) In the display device according to Item (15) or (16), the optical film may be disposed so as to reach an outside of the region surrounded by the sealing member.

(18) In the display device according to any one of Items (1) to (17), the optical film may be made of a material selected from the group consisting of ZnO, ZnCrO$_4$, and Al$_2$O$_3$.

(19) In the display device according to any one of Items (1) to (18): the display device may further include a backlight unit; the plurality of shutters may each have at least one opening; and the plurality of shutters may be mechanically movable and may control transmission and blocking of light from the backlight unit.

BRIEF DESCRIPTION OF THE DRAWINGS

In the accompanying drawings.

DETAILED DESCRIPTION OF THE INVENTION

Figure 1:
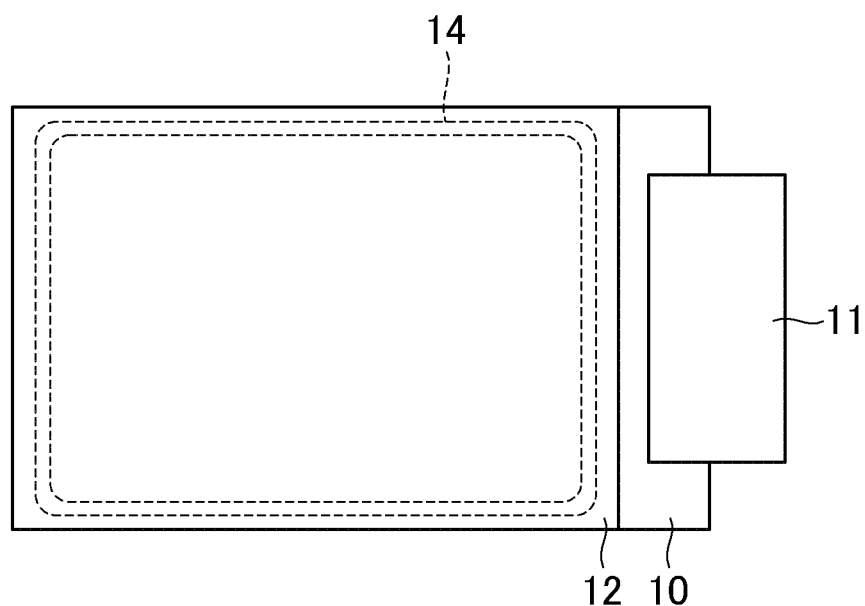
FIG. 1 is a plan view of a display device according to a first embodiment of the present invention.
Figure 2:
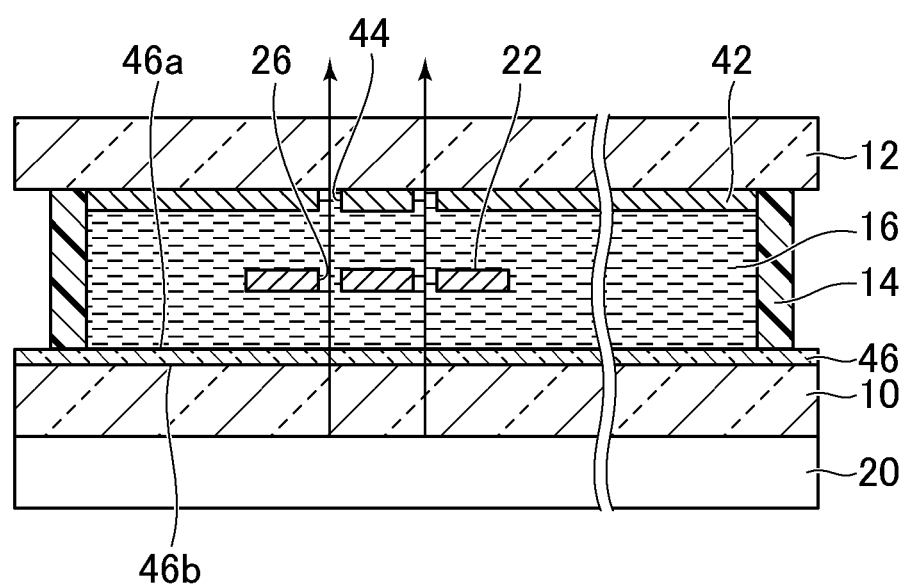
FIG. 2 is a cross-sectional view illustrating an outline of the display device according to the first embodiment of the present invention.

Hereinafter, embodiments of the present invention are described with reference to the drawings.
[First Embodiment]
FIG. 1 is a plan view of a display device according to a first embodiment of the present invention. FIG. 2 is a cross-sectional view illustrating an outline of the display device according to the first embodiment of the present invention.

The display device includes a pair of light transmissive substrates 10 and 12 (insulating substrates, for example, glass substrates). The pair of light transmissive substrates 10 and 12 is disposed so as to be opposed to each other at an interval. On the one light transmissive substrate 10, there is disposed a flexible wiring board 11 for electrical connection.

The display device includes a sealing member 14 that bonds the pair of light transmissive substrates 10 and 12 together and defines an encapsulation space between the pair of light transmissive substrates 10 and 12. As illustrated in FIG. 1, the sealing member 14 is disposed so as to avoid the periphery (the entire periphery in FIG. 1) of the pair of light transmissive substrates 10 and 12. The periphery (for example, the entire periphery) of the pair of light transmissive substrates 10 and 12 extends outward from the sealing member 14. Liquid 16 having optical isotropy is filled in the encapsulation space. It is preferred to use silicone oil for the liquid 16, for example. Liquid crystal having optical anisotropy is not included in the liquid 16.

The display device includes a backlight unit 20 and a plurality of shutters 22 disposed in the encapsulation space so as to optically display an image. The shutter 22 mechanically controls transmission and blocking of light from the backlight unit 20.

Figure 3:
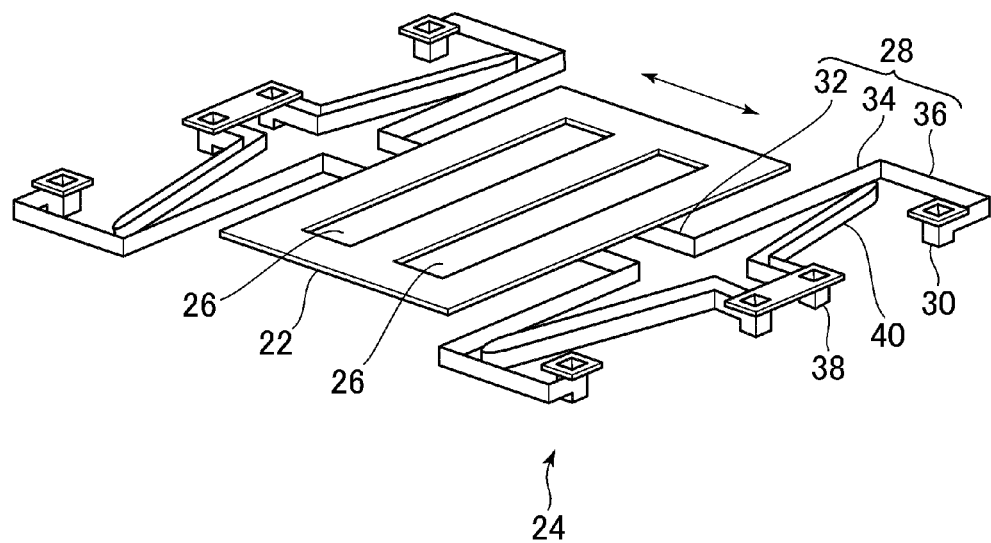
FIG. 3 is a diagram illustrating a shutter and a drive unit for the same.

FIG. 3 is a diagram illustrating the shutter 22 and a drive unit 24 for driving the shutter 22. The shutter 22 and the drive unit 24 are disposed in the liquid 16. The liquid 16 can suppress undesired vibration and vibration noise due to movement of the shutter 22 and the drive unit 24.

The shutter 22 illustrated in FIG. 3 is provided on one light transmissive substrate 10 (for example, on a lower side in FIG. 2). The shutter 22 is a plate including a drive aperture 26. Light is allowed to pass through the drive aperture 26, and is blocked at a part other than the drive aperture 26. The drive aperture 26 has a shape long in one direction. Note that, as illustrated in FIG. 2, light is supplied from the backlight unit 20 lying under the light transmissive substrate 10. In FIG. 2, the backlight unit 20 is disposed so as to be opposed to the light transmissive substrate 10 on which the shutter 22 is provided, but may be disposed so as to be opposed to the other light transmissive substrate 12.

The shutter 22 is supported by a first spring 28 to be suspended above the light transmissive substrate 10, that is, the shutter 22 is disposed so as to have a predetermined gap with respect to a main surface of the light transmissive substrate 10. A plurality of (four in FIG. 3) first springs 28 support the shutter 22. The first spring 28 is fixed to the light transmissive substrate 10 by a first anchor portion 30.

The first spring 28 is made of an elastically deformable material, and is disposed so as to be deformable in a direction parallel to a plate surface (main surface of the plate) of the shutter 22. Specifically, the first spring 28 includes a first portion 32 extending in a direction separating from the shutter 22 (direction intersecting (for example, orthogonal to) a longitudinal direction of the drive aperture 26), a second portion 34 extending in a direction along the longitudinal direction of the drive aperture portion 26 outwardly from a center of the drive aperture 26 in the longitudinal direction, and a third portion 36 further extending in the direction separating from the shutter 22 (direction intersecting (for example, orthogonal to) the longitudinal direction of the drive aperture 26). Further, as indicated by arrows in FIG. 3, the shutter 22 is movable in the direction intersecting (for example, orthogonal to) the longitudinal direction of the drive aperture 26.

The light transmissive substrate 10 is provided with a second spring 40 supported by a second anchor portion 38. The second spring 40 is opposed to the second portion 34 of the first spring 28 on a side separated from the shutter 22 with respect to the second portion 34. When a voltage is applied to the second anchor portion 38, due to the electrostatic attractive force caused by a potential difference between the second anchor portion 38 and the second portion 34 of the first spring 28, the second portion 34 is attracted toward the second spring 40. When the second portion 34 is attracted, the shutter 22 is also attracted via the first portion 32 provided integrally with the second portion 34. That is, the first spring 28 and the second spring 40 are provided for constituting a drive unit 24 for mechanically driving the shutter 22.

The other light transmissive substrate 12 has a light shielding film 42 formed thereon as illustrated in FIG. 2. In the light shielding film 42, a fixed aperture 44 is formed. Light is allowed to pass when the above-mentioned drive aperture 26 of the shutter 22 and the fixed aperture 44 of the light shielding film 42 communicate with each other, and light is blocked when the fixed aperture 44 of the light shielding film 42 is covered due to the movement of the shutter 22. In other words, the shutter 22 is mechanically driven so as to control passage and blocking of light through the fixed aperture 44 of the light shielding film 42. The drive aperture 26 of the shutter 22 and the fixed aperture 44 of the light shielding film 42 corresponding to each other constitute one pixel, and an image is displayed by a large number of pixels. Therefore, a plurality of (large number of) shutters 22 are provided to the light transmissive substrate 10.

As illustrated in FIG. 2, the display device includes an optical film 46. The optical film 46 is disposed between the liquid 16 and at least one of the pair of light transmissive substrates 10 and 12. The optical film 46 is formed of a single layer. One surface of the optical film 46 is provided in contact with the liquid 16. The other surface of the optical film 46 is provided in contact with one of the pair of light transmissive substrates 10 and 12. Specifically, the optical film 46 is disposed so that a lower surface 46b thereof is adjacent to the one light transmissive substrate 10.

The optical film 46 is made of a material selected from the group consisting of ZnO, $ZnCrO_4$, and $Al_2O_3$, for example. The refractive index of the optical film 46 is different from the refractive index of the one light transmissive substrate 10 provided in contact with the optical film 46. The refractive index of the optical film 46 is larger than any one of refractive indices of the one light transmissive substrate 10 provided in contact with the optical film 46, the air, and the liquid 16.

As illustrated in FIG. 2, the optical film 46 is disposed at least in a part adjacent to the sealing member 14 in a region surrounded by the sealing member 14. The optical film 46 is disposed in the entire region surrounded by the sealing member 14. Further, the optical film 46 is disposed so as to reach the outside of the region surrounded by the sealing member 14.

Figure 4:
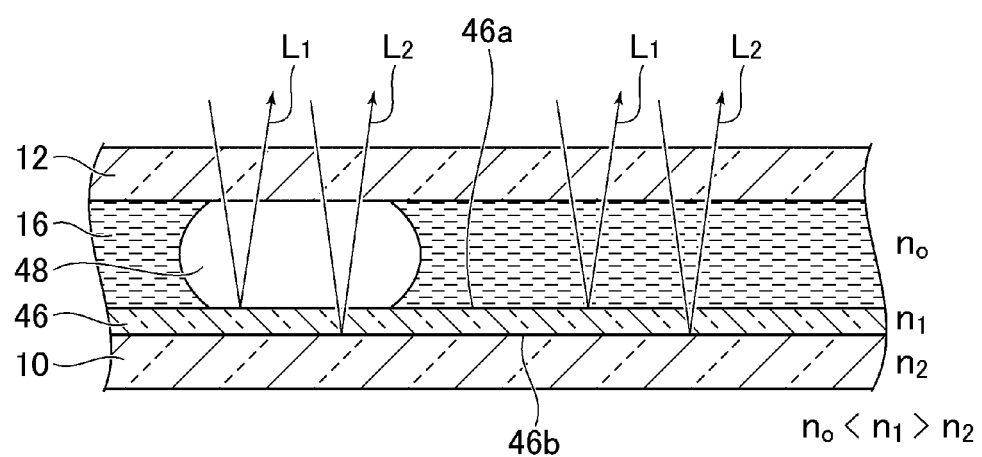
FIG. 4 is a diagram illustrating action and effect of the display device according to the first embodiment of the present invention.

FIG. 4 is a diagram illustrating action and effect of the display device. FIG. 4 illustrates a cross-section inside the drive aperture 26 and the fixed aperture 44 that communicate with each other illustrated in FIG. 2. In this example, the liquid 16 includes an air bubble 48. According to this embodiment, the air bubble 48 can be inspected easily, and the action thereof is described below.

When natural light irradiates the upper surface of the optical film 46, reflection light that is reflected by an upper surface 46a and propagates and reflection light that enters the optical film 46 and is reflected by the lower surface 46b so as to exit from the upper surface 46a interfere with each other.

Here, $n_0 < n_1$ and $n_2 < n_1$ hold, where $n_0$ represents a refractive index of a substance adjacent to the upper surface 46a of the optical film 46 (liquid 16 or air of the air bubble 48), $n_1$ represents a refractive index of the optical film 46, and $n_2$ represents a refractive index of one light transmissive substrate provided in contact with the optical film 46.

The natural light includes a light ray group including light rays having different wavelengths and different incident angles to the optical film 46. A light ray group having a wavelength $\lambda_0$ included in the natural light includes first light rays $L_1$ reflected by the upper surface 46a of the optical film 46 and second light rays $L_2$ reflected by the lower surface 46b of the optical film 46 so as to exit from the upper surface 46a. Note that, it is supposed that the first light rays $L_1$ and the second light rays $L_2$ are normal incident light, but those rays are illustrated as entering at an inclined angle for easy viewing in FIG. 4. The first light ray $L_1$ and the second light ray $L_2$ passing through the liquid 16 interfere with each other as a pair, while the first light ray $L_1$ and the second light ray $L_2$ passing through the air bubble 48 (air) interfere with each other as a pair.

When an optical path difference ((actual distance difference)×(refractive index)) between the pair of the first light ray $L_1$ and the second light ray $L_2$ passing through each of the liquid 16 and the air bubble 48 (air) is an odd multiple of half the wavelength $\lambda_0$, the reflection factor of the first light ray $L_1$ and the second light ray $L_2$ becomes a maximum value determined by $Rmax = ((n_0 n_2 - n_1^2)/(n_0 n_2 + n_1^2))^2$.

When the optical path difference between the pair of the first light ray $L_1$ and the second light ray $L_2$ passing through each of the liquid 16 and the air bubble 48 (air) is an integral multiple of the wavelength $\lambda_0$, the reflection factor of the first light ray $L_1$ and the second light ray $L_2$ becomes a minimum value determined by $Rmin = ((n_0 - n_2)/(n_0 + n_2))^2$.

The reflection factor of natural light when the natural light passes through the liquid 16 is in the range from a minimum reflection factor $R_{LIQUID}min$ to a maximum reflection factor $R_{LIQUID}max$ obtained by substituting the refractive index of the liquid 16 into $n_0$ in the above-mentioned equations for determining the minimum value and the maximum value.

The reflection factor of the natural light when the liquid 16 includes the air bubble 48 on the optical film 46 and the natural light passes through the air bubble 48 is in the range from a minimum reflection factor $R_{Air}min$ to a maximum reflection factor $R_{Air}max$ obtained by substituting the refractive index of the air into $n_0$ in the above-mentioned equations for determining the minimum value and the maximum value.

For instance, it is supposed that the refractive index of the air bubble 48 (air) is 1.00, the refractive index of the liquid 16 is 1.37, the refractive index of the optical film 46 is 1.80, and the refractive index of the light transmissive substrate (glass substrate) is 1.52. Then, the range of the reflection factor is as shown in the table below.

TABLE 1

|  | Without optical film | With optical film |
|---|---|---|
| Liquid (average value in parentheses) | 0.5 to 12% (6.25%) | 0.5 to 5% (2.75%) |
| Air bubble (average value in parentheses) | 4% (4%) | 5 to 13% (9%) |
| Difference of average value | 2.25% | 6.25% |

The average value of 9% when the natural light passes through the air bubble 48 (air) is larger than twice the average value of 2.75% when the natural light passes through the liquid 16. Therefore, according to this embodiment, it is easier to inspect the air bubble 48 owing to the difference of reflection factor.

In contrast, in the conventional structure without the optical film 46, there is a small difference between the average value of 4% of the reflection factor when the natural light passes through the air bubble 48 (air) and the average value of 6.25% of the reflection factor when the natural light passes through the liquid 16. Therefore, it is understood that it is difficult to inspect the air bubble 48 with a difference of reflection factor.

Note that, the optical film 46 is also formed in a part of the light transmissive substrate extending outward from the sealing member 14, as illustrated in FIG. 2. This part is outside the region surrounded by the sealing member 14, and therefore, originally, there is no liquid 16, and hence the air is adjacent to the optical film 46 in the same manner as the air bubble 48. Therefore, because the reflection factor in the region outside the sealing member 14 is the same as the reflection factor of the region where the air bubble 48 is generated, this part can be used as a reference when inspecting presence of the air bubble 48.

[Second Embodiment]

Figure 5:
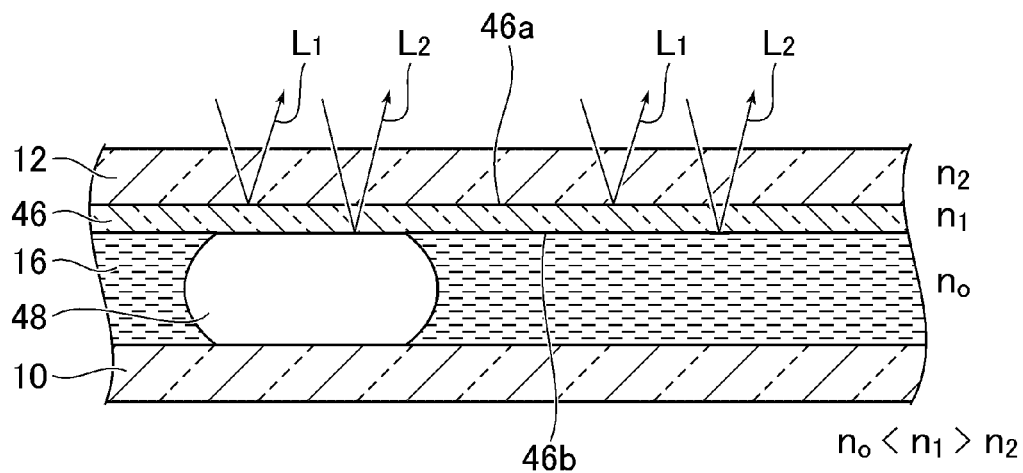
FIG. 5 is a diagram illustrating action and effect of a display device according to a second embodiment of the present invention.

FIG. 5 is a diagram illustrating action and effect of a display device according to a second embodiment of the present invention. In this example, the optical film 46 is disposed so that the upper surface 46a thereof is adjacent to one light transmissive substrate 12. Further, when natural light irradiates the upper surface 46a of the optical film 46, reflection light that is reflected by the upper surface 46a of the optical film 46 and propagates interferes with reflection light that enters the optical film 46 and is reflected by the lower surface 46b so as to exit from the upper surface 46a.

In this example, $n_0 < n_1$ and $n_2 < n_1$ hold, where $n_0$ represents a refractive index of a substance adjacent to the lower surface 46b of the optical film 46, $n_1$ represents a refractive index of the optical film 46, and $n_2$ represents a refractive index of the one light transmissive substrate provided in contact with the optical film 46.

The natural light includes a light ray group including light rays having different wavelengths and different incident angles to the optical film 46. A light ray group having a wavelength $\lambda_0$ included in the natural light includes first light rays $L_1$ reflected by the upper surface 46a and second light rays $L_2$ reflected by the lower surface 46b so as to exit from the upper surface 46a.

When an optical path difference between the first light ray $L_1$ and the second light ray $L_2$ is an odd multiple of half the wavelength $\lambda_0$, the reflection factor of the first light ray $L_1$ and the second light ray $L_2$ becomes a maximum value determined by $Rmax=((n_2 n_0 - n_1^2)/(n_2 n_0 + n_1^2))^2$.

When an optical path difference between the first light ray $L_1$ and the second light ray $L_2$ is an integral multiple of the wavelength $\lambda_0$, the reflection factor of the first light ray $L_1$ and the second light ray $L_2$ becomes a minimum value determined by $Rmin=((n_2 - n_0)/(n_2 + n_0))^2$.

The reflection factor of the natural light when the natural light is reflected by the upper surface 46a and the lower surface 46b above the liquid 16 is in the range from a minimum reflection factor $R_{LIQUID}min$ to a maximum reflection factor $R_{LIQUID}max$ obtained by substituting the refractive index of the liquid 16 into $n_0$ in the equations for determining the minimum value and the maximum value.

The reflection factor of the natural light when the liquid 16 includes the air bubble 48 on the optical film 46 and the natural light is reflected by the upper surface 46a and the lower surface 46b above the air bubble 48 is in the range from a minimum reflection factor $R_{Air}min$ to a maximum reflection factor $R_{Air}max$ obtained by substituting the refractive index of the air into $n_0$ in the equations for determining the minimum value and the maximum value.

The average value of the minimum reflection factor $R_{Air}min$ and the maximum reflection factor $R_{Air}max$ is larger than twice the average value of the minimum reflection factor $R_{LIQUID}min$ and the maximum reflection factor $R_{LIQUID}max$.

Therefore, the effect described above in the first embodiment can also be achieved in this embodiment.

[Third Embodiment]

Figure 6:
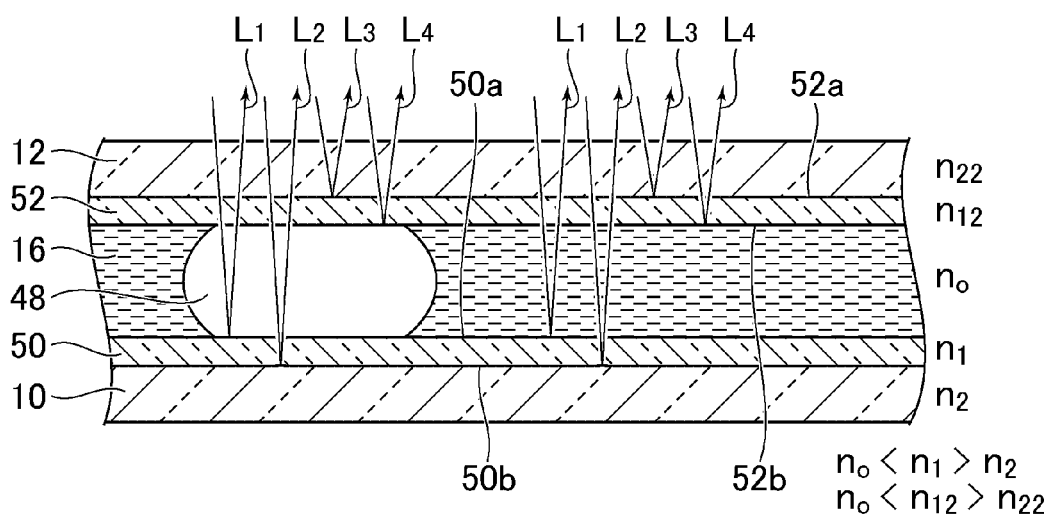
FIG. 6 is a diagram illustrating action and effect of a display device according to a third embodiment of the present invention.

FIG. 6 is a diagram illustrating action and effect of a display device according to a third embodiment of the present invention. In this example, the optical film includes a first optical film 50 and a second optical film 52. Each of the first optical film 50 and the second optical film 52 has an upper surface 50a or 52a and a lower surface 50b or 52b. One light transmissive substrate 10 is adjacent to the lower surface 50b of the first optical film 50. The other light transmissive substrate 12 is adjacent to the upper surface 52a of the second optical film 52.

When natural light irradiates the upper surfaces 50a and 52a of the first optical film 50 and the second optical film 52, respectively, reflection light that is reflected by the upper surface 50a of the first optical film 50 and propagates interferes with reflection light that enters the first optical film 50 and is reflected by the lower surface 50b of the first optical film 50 so as to exit from the upper surface 50a of the first optical film 50. Further, reflection light that is reflected by the upper surface 52a of the second optical film 52 and propagates interferes with reflection light that enters the second optical film 52 and is reflected by the lower surface 52b of the second optical film 52 so as to exit from the upper surface 52a of the second optical film 52.

Here, $n_0 < n_1$ and $n_2 < n_1$ hold, where $n_0$ represents a refractive index of a substance adjacent to the upper surface 50a of the first optical film 50 and the lower surface 52b of the second optical film 52, $n_1$ represents a refractive index of the first optical film 50, and $n_2$ represents a refractive index of the one light transmissive substrate 10 provided in contact with the first optical film 50.

Further, $n_0 < n_{12}$ and $n_{22} < n_{12}$ hold, where $n_{12}$ represents a refractive index of the second optical film 52, and $n_{22}$ represents a refractive index of the other light transmissive substrate 12 provided in contact with the second optical film 52.

The natural light includes a light ray group including light rays having different wavelengths and different incident angles to the first optical film 50 and the second optical film 52. A light ray group having a wavelength $\lambda_0$ included in the natural light includes first light rays $L_1$ reflected by the upper surface 50a of the first optical film 50, second light rays $L_2$ reflected by the lower surface 50b of the first optical film 50 so as to exit from the upper surface 50a of the first optical film 50, third light rays $L_3$ reflected by the upper surface 52a of the second optical film 52, and fourth light rays $L_4$ reflected by the lower surface 52b of the second optical film 52 so as to exit from the upper surface 52a.

The first light ray $L_1$ and the second light ray $L_2$ passing through the liquid 16 interfere with each other as a pair, while the first light ray $L_1$ and the second light ray $L_2$ passing through the air bubble 48 (air) interfere with each other as a pair. In addition, the third light ray $L_3$ and the fourth light ray $L_4$ above the liquid 16 interfere with each other as a pair, while the third light ray $L_3$ and the fourth light ray $L_4$ above the air bubble 48 (air) interfere with each other as a pair.

When an optical path difference between the pair of the first light ray $L_1$ and the second light ray $L_2$ passing through each of the liquid 16 and the air bubble 48 (air) is an odd multiple of half the wavelength $\lambda_0$, the reflection factor of the first light ray $L_1$ and the second light ray $L_2$ on the upper surface 50a and the lower surface 50b of the first optical film 50 becomes a first maximum value determined by $Rmax=((n_0 n_2 - n_1^2)/(n_0 n_2 + n_1^2))^2$.

When the optical path difference between the pair of the first light ray $L_1$ and the second light ray $L_2$ passing through each of the liquid 16 and the air bubble 48 (air) is an integral multiple of the wavelength $\lambda_0$, the reflection factor of the first light ray $L_1$ and the second light ray $L_2$ on the upper surface 50a and the lower surface 50b of the first optical film 50 becomes a first minimum value determined by $Rmin=((n_0-n_2)/(n_0+n_2))^2$.

The reflection factor of natural light on the upper surface 50a and the lower surface 50b of the first optical film 50 when the natural light passes through the liquid 16 is in the range from a minimum reflection factor $R_{LIQUID}\text{min}$ to a maximum reflection factor $R_{LIQUID}\text{max}$ obtained by substituting the refractive index of the liquid 16 into $n_0$ in the equations for determining the first minimum value and the first maximum value.

The reflection factor of the natural light on the upper surface 50a and the lower surface 50b of the first optical film 50 when the liquid 16 includes the air bubble 48 on the first optical film 50 and the natural light passes through the air bubble 48 is in the range from a minimum reflection factor $R_{Air}\text{min}$ to a maximum reflection factor $R_{Air}\text{max}$ obtained by substituting the refractive index of the air into $n_0$ in the equations for determining the first minimum value and the first maximum value.

The average value of the minimum reflection factor $R_{Air}\text{min}$ and the maximum reflection factor $R_{Air}\text{max}$ is larger than twice the average value of the minimum reflection factor $R_{LIQUID}\text{min}$ and the maximum reflection factor $R_{LIQUID}\text{max}$.

When an optical path difference between the pair of the third light ray $L_3$ and the fourth light ray $L_4$ reflected by the upper surface 52a and the lower surface 52b above the liquid 16 and the air bubble 48 (air) is an odd multiple of half the wavelength $\lambda_0$, the reflection factor of the third light ray $L_3$ and the fourth light ray $L_4$ on the upper surface 52a and the lower surface 52b of the second optical film 52 becomes a second maximum value determined by $Rmax_2=(n_{22}n_0-n_{12}^2)/(n_{22}n_0+n_{12}^2))^2$.

When the optical path difference between the pair of the third light ray $L_3$ and the fourth light ray $L_4$ reflected by the upper surface 52a and the lower surface 52b above the liquid 16 and the air bubble 48 (air) is an integral multiple of the wavelength $\lambda_0$, the reflection factor of the third light ray $L_3$ and the fourth light ray $L_4$ on the upper surface 52a and the lower surface 52b of the second optical film 52 becomes a second minimum value determined by $Rmin_2=((n_{22}-n_0)/(n_{22}+n_0))^2$.

The reflection factor of natural light on the upper surface 52a and the lower surface 52b of the second optical film 52 when the natural light is reflected above the liquid 16 is in the range from a minimum reflection factor $R_{LIQUID}\text{min}_2$ to a maximum reflection factor $R_{LIQUID}\text{max}_2$ obtained by substituting the refractive index of the air into $n_0$ in the equations for determining the second minimum value and the second maximum value.

The reflection factor of natural light on the upper surface 52a and the lower surface 52b of the second optical film 52 when the natural light is reflected above the air bubble 48 is in the range from a minimum reflection factor $R_{AIR}\text{min}_2$ to a maximum reflection factor $R_{AIR}\text{max}_2$ obtained by substituting the refractive index of the air into $n_0$ in the equations for determining the second minimum value and the second maximum value.

The average value of the minimum reflection factor $R_{Air}\text{min}_2$ and the maximum reflection factor $R_{Air}\text{max}_2$ is larger than twice the average value of the minimum reflection factor $R_{LIQUID}\text{min}_2$ and the maximum reflection factor $R_{LIQUID}\text{max}_2$.

Therefore, the effect described above in the first embodiment can also be achieved in this embodiment.

[Modifications]

Figure 7:
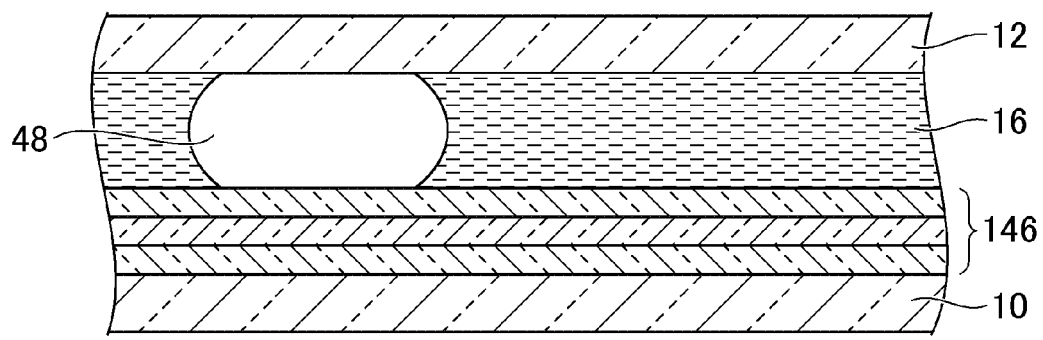
FIG. 7 is a diagram illustrating a first modification of the embodiments of the present invention.

FIG. 7 is a diagram illustrating a first modification of the embodiments of the present invention. In this example, an optical film 146 is formed of a plurality of layers. This optical film 146 formed of the plurality of layers can be applied to any one of the above-mentioned first to third embodiments.

Figure 8:
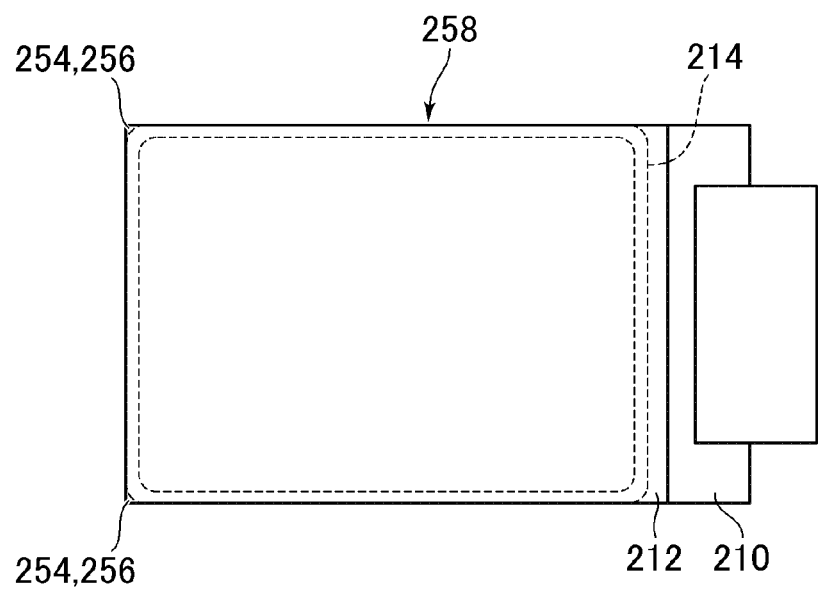
FIG. 8 is a diagram illustrating a second modification of the embodiments of the present invention.

FIG. 8 is a diagram illustrating a second modification of the embodiments of the present invention. In this example, a sealing member 214 is disposed so as to avoid a first part 254 in the periphery of a pair of light transmissive substrates 210 and 212. The pair of light transmissive substrates 210 and 212 has a rectangular shape in plan view, and the sealing member 214 is disposed so as to avoid at least one corner 256 (or all corners 256) of the pair of light transmissive substrates 210 and 212. The first part 254 (the corner 256) in the periphery of the pair of light transmissive substrates 210 and 212 extends outward from the sealing member 214. The sealing member 214 is disposed so as to pass a second part 258 in the periphery of the pair of light transmissive substrates 210 and 212. The second part 258 may be the entire remaining part of the periphery after the first part 254 is excluded, or a part of the remaining part of the periphery after the first part 254 is excluded. With this structure, it is possible to form a region to be a reference when an air bubble exists (region without liquid) outside the sealing member 214 while using a wide region of the light transmissive substrate as a display region.

While there have been described what are at present considered to be certain embodiments of the invention, it will be understood that various modifications may be made thereto, and it is intended that the appended claims cover all such modifications as fall within the true spirit and scope of the invention.

What is claimed is:

1. A display device, comprising:
   a pair of light transmissive substrates disposed to be opposed to each other at an interval;
   a sealing member which bonds the pair of light transmissive substrates together and defines an encapsulation space between the pair of light transmissive substrates;
   a plurality of shutters disposed in the encapsulation space so as to optically display an image;
   liquid having optical isotropy filled in the encapsulation space; and
   an optical film disposed between the liquid and at least one of the pair of light transmissive substrates, wherein:
   one surface of the optical film is provided in contact with the liquid;
   another surface of the optical film is provided in contact with one of the pair of light transmissive substrates; and
   a refractive index of the optical film is different from a refractive index of the one of the pair of light transmissive substrates provided in contact with the optical film.

2. The display device according to claim 1, wherein the optical film is formed of a single layer.

3. The display device according to claim 1, wherein the optical film is formed of a plurality of layers.

4. The display device according to claim 1, wherein the refractive index of the optical film is larger than the refractive index of the one of the pair of light transmissive substrates provided in contact with the optical film and is larger than refractive indices of air and the liquid.

5. The display device according to claim 1, wherein:
   the optical film is disposed so that a lower surface thereof is adjacent to the one of the pair of light transmissive substrates; and
   when natural light irradiates an upper surface of the optical film, reflection light that is reflected by the upper surface and propagates interferes with reflection light that enters the optical film and is reflected by the lower surface so as to exit from the upper surface.

6. The display device according to claim 5, wherein:
   the following expressions hold:

$n_0 < n_1$ and $n_2 < n_1$, where $n_0$ represents a refractive index of a substance adjacent to the upper surface of the optical film, $n_1$ represents the refractive index of the optical film, and $n_2$ represents the refractive index of the one of the pair of light transmissive substrates provided in contact with the optical film;
   the natural light comprises a light ray group including light rays having different wavelengths and different incident angles to the optical film;
   a light ray group having a wavelength $\lambda_0$ included in the natural light comprises a first light ray reflected by the upper surface and a second light ray reflected by the lower surface so as to exit from the upper surface;
   when an optical path difference between the first light ray and the second light ray is an odd multiple of half the wavelength $\lambda_0$, a reflection factor of the first light ray and the second light ray becomes a maximum value determined by $Rmax = ((n_0 n_2 - n_1^2)/(n_0 n_2 + n_1^2))^2$;
   when the optical path difference between the first light ray and the second light ray is an integral multiple of the wavelength $\lambda_0$, the reflection factor of the first light ray and the second light ray becomes a minimum value determined by $Rmin = ((n_0 - n_2)/(n_0 + n_2))^2$;
   a reflection factor of the natural light when the natural light passes through the liquid is in a range from a minimum reflection factor $R_{LIQUID}min$ to a maximum reflection factor $R_{LIQUID}max$ obtained by substituting a refractive index of the liquid into $n_0$ in equations for determining the minimum value and the maximum value;
   a reflection factor of the natural light when the liquid includes an air bubble on the optical film and the natural light passes through the air bubble is in a range from a minimum reflection factor $R_{Air}min$ to a maximum reflection factor $R_{Air}max$ obtained by substituting a refractive index of air into $n_0$ in the equations for determining the minimum value and the maximum value; and
   one of an average value of the minimum reflection factor $R_{Air}min$ and the maximum reflection factor $R_{Air}max$ and an average value of the minimum reflection factor $R_{LIQUID}min$ and the maximum reflection factor $R_{LIQUID}max$ is larger than twice another thereof.

7. The display device according to claim 1, wherein:
   the optical film is disposed so that an upper surface thereof is adjacent to the one of the pair of light transmissive substrates; and
   when natural light irradiates the upper surface, reflection light that is reflected by the upper surface and propagates interferes with reflection light that enters the optical film and is reflected by a lower surface of the optical film so as to exit from the upper surface.

8. The display device according to claim 7, wherein:
   the following expressions hold:

$n_0 < n_1$ and $n_2 < n_1$, where $n_0$ represents a refractive index of a substance adjacent to the lower surface of the optical film, $n_1$ represents the refractive index of the optical film, and $n_2$ represents the refractive index of the one of the pair of light transmissive substrates provided in contact with the optical film;
   the natural light comprises a light ray group including light rays having different wavelengths and different incident angles to the optical film;
   a light ray group having a wavelength $\lambda_0$ included in the natural light comprises a first light ray reflected by the upper surface and a second light ray reflected by the lower surface so as to exit from the upper surface;
   when an optical path difference between the first light ray and the second light ray is an odd multiple of half the wavelength $\lambda_0$, a reflection factor of the first light ray and the second light ray becomes a maximum value determined by $Rmax = ((n_2 n_0 - n_1^2)/(n_2 n_0 + n_1^2))^2$;
   when the optical path difference between the first light ray and the second light ray is an integral multiple of the wavelength $\lambda_0$, the reflection factor of the first light ray and the second light ray becomes a minimum value determined by $Rmin = ((n_2 - n_0)/(n_2 + n_0))^2$;
   a reflection factor of the natural light when the natural light is reflected by the upper surface and the lower surface above the liquid is in a range from a minimum reflection factor $R_{LIQUID}min$ to a maximum reflection factor $R_{LIQUID}max$ obtained by substituting a refractive index of the liquid into $n_0$ in equations for determining the minimum value and the maximum value;
   a reflection factor of the natural light when the liquid includes an air bubble on the optical film and the natural light is reflected by the upper surface and the lower surface above the air bubble is in a range from a minimum reflection factor $R_{Air}min$ to a maximum reflection factor $R_{Air}max$ obtained by substituting a refractive index of air into $n_0$ in the equations for determining the minimum value and the maximum value; and one of an average value of the minimum reflection factor $R_{Air}$min and the maximum reflection factor $R_{Air}$max and an average value of the minimum reflection factor $R_{LIQUID}$min and the maximum reflection factor $R_{LIQUID}$max is larger than twice another thereof.

9. The display device according to claim 1, wherein:
the optical film comprises a first optical film and a second optical film;
each of the first optical film and the second optical film has an upper surface and a lower surface;
the lower surface of the first optical film is adjacent to one of the pair of light transmissive substrates;
the upper surface of the second optical film is adjacent to another of the pair of light transmissive substrates; and
when natural light irradiates each of the upper surface of the first optical film and the upper surface of the second optical film, reflection light that is reflected by the upper surface of the first optical film and propagates interferes with reflection light that enters the first optical film and is reflected by the lower surface of the first optical film so as to exit from the upper surface of the first optical film, while reflection light that is reflected by the upper surface of the second optical film and propagates interferes with reflection light that enters the second optical film and is reflected by the lower surface of the second optical film so as to exit from the upper surface of the second optical film.

10. The display device according to claim 9, wherein:
the following expressions hold:

$$n_0 < n_1 \text{ and } n_2 < n_1,$$

where $n_0$ represents a refractive index of a substance adjacent to the upper surface of the first optical film and the lower surface of the second optical film, $n_1$ represents a refractive index of the first optical film, and $n_2$ represents a refractive index of the one of the pair of light transmissive substrates provided in contact with the first optical film;
the following expressions hold:

$$n_0 < n_{12} \text{ and } n_{22} < n_{12},$$

where $n_{12}$ represents a refractive index of the second optical film, and $n_{22}$ represents a refractive index of the another of the pair of light transmissive substrates provided in contact with the second optical film;
the natural light comprises a light ray group including light rays having different wavelengths and different incident angles to the first optical film and the second optical film;
a light ray group having a wavelength $\lambda_0$ included in the natural light comprises a first light ray reflected by the upper surface of the first optical film, a second light ray reflected by the lower surface of the first optical film so as to exit from the upper surface of the first optical film, a third light ray reflected by the upper surface of the second optical film, and a fourth light ray reflected by the lower surface of the second optical film so as to exit from the upper surface of the second optical film;
when an optical path difference between the first light ray and the second light ray is an odd multiple of half the wavelength $\lambda_0$, a reflection factor of the first light ray and the second light ray on the upper surface and the lower surface of the first optical film becomes a first maximum value determined by $Rmax=((n_0 n_2 - n_1^2)/(n_0 n_2 + n_1^2))^2$;
when the optical path difference between the first light ray and the second light ray is an integral multiple of the wavelength $\lambda_0$, the reflection factor of the first light ray and the second light ray on the upper surface and the lower surface of the first optical film becomes a first minimum value determined by $Rmin=((n_0-n_2)/(n_0+n_2))^2$;
a reflection factor of the natural light on the upper surface and the lower surface of the first optical film when the natural light passes through the liquid is in a range from a minimum reflection factor $R_{LIQUID}$min to a maximum reflection factor $R_{LIQUID}$max obtained by substituting a refractive index of the liquid into $n_0$ in equations for determining the first minimum value and the first maximum value;
a reflection factor of the natural light on the upper surface and the lower surface of the first optical film when the liquid includes an air bubble on the first optical film and the natural light passes through the air bubble is in a range from a minimum reflection factor $R_{Air}$min to a maximum reflection factor $R_{Air}$max obtained by substituting a refractive index of air into $n_0$ in the equations for determining the first minimum value and the first maximum value;
an average value of the minimum reflection factor $R_{Air}$min and the maximum reflection factor $R_{Air}$max is larger than twice an average value of the minimum reflection factor $R_{LIQUID}$min and the maximum reflection factor $R_{LIQUID}$max;
when an optical path difference between the third light ray and the fourth light ray is an odd multiple of half the wavelength $\lambda_0$, a reflection factor of the third light ray and the fourth light ray on the upper surface and the lower surface of the second optical film becomes a second maximum value determined by $Rmax_2=((n_{22}n_0-n_{12}^2)/(n_{22}n_0+n_{12}^2))^2$;
when the optical path difference between the third light ray and the fourth light ray is an integral multiple of the wavelength $\lambda_0$, the reflection factor of the third light ray and the fourth light ray on the upper surface and the lower surface of the second optical film becomes a second minimum value determined by $Rmin_2=((n_{22}-n_0)/(n_{22}+n_0))^2$; a reflection factor of the natural light on the upper surface and the lower surface of the second optical film when the natural light is reflected above the liquid is in a range from a minimum reflection factor $R_{LIQUID}$min$_2$ to a maximum reflection factor $R_{LIQUID}$max$_2$ obtained by substituting the refractive index of the air into $n_0$ in equations for determining the second minimum value and the second maximum value;
a reflection factor of the natural light on the upper surface and the lower surface of the second optical film when the natural light is reflected above the air bubble is in a range from a minimum reflection factor $R_{Air}$min$_2$ to a maximum reflection factor $R_{Air}$max$_2$ obtained by substituting the refractive index of the air into $n_0$ in the equations for determining the second minimum value and the second maximum value; and
one of an average value of the minimum reflection factor $R_{Air}$min$_2$ and the maximum reflection factor $R_{Air}$max$_2$ and an average value of the minimum reflection factor $R_{LIQUID}$min$_2$ and the maximum reflection factor $R_{LIQUID}$max$_2$ is larger than twice another thereof.

11. The display device according to claim 1, wherein:
the sealing member is disposed so as to avoid a periphery of the pair of light transmissive substrates; and
the periphery of the pair of light transmissive substrates extends outward from the sealing member.

12. The display device according to claim 11, wherein:
the sealing member is disposed so as to avoid an entirety of the periphery of the pair of light transmissive substrates, and
the entirety of the periphery of the pair of light transmissive substrates extends outward from the sealing member.

13. The display device according to claim 11, wherein:
the sealing member is disposed so as to avoid a first part in the periphery of the pair of light transmissive substrates, and so as to pass a second part in the periphery of the pair of light transmissive substrates; and
the first part in the periphery of the pair of light transmissive substrates extends outward from the sealing member.

14. The display device according to claim 1, wherein:
each of the pair of light transmissive substrates has a rectangular shape in plan view;
the sealing member is disposed so as to avoid a corner of the pair of light transmissive substrates; and
the corner of the pair of light transmissive substrates extends outward from the sealing member.

15. The display device according to claim 1, wherein the optical film is disposed at least in a part adjacent to the sealing member in a region surrounded by the sealing member.

16. The display device according to claim 15, wherein the optical film is disposed in an entire region surrounded by the sealing member.

17. The display device according to claim 15, wherein the optical film is disposed so as to reach an outside of the region surrounded by the sealing member.

18. The display device according to claim 1, wherein the optical film is made of a material selected from the group consisting of $ZnO$, $ZnCrO_4$, and $Al_2O_3$.

19. The display device according to claim 1, further comprising a backlight unit, wherein:
the plurality of shutters each have at least one aperture; and
the plurality of shutters are mechanically movable and control transmission and blocking of light from the backlight unit.

* * * * *